United States Patent
McQueen et al.

(10) Patent No.: US 8,123,739 B2
(45) Date of Patent: Feb. 28, 2012

(54) DRAINAGE CATHETER AND METHOD FOR CATHETERIZING A PATIENT

(75) Inventors: Amy McQueen, Bloomington, IN (US); Michael D. Deckard, Solsberry, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 546 days.

(21) Appl. No.: 12/193,847

(22) Filed: Aug. 19, 2008

(65) Prior Publication Data

US 2010/0049171 A1 Feb. 25, 2010

(51) Int. Cl.
*A61M 27/00* (2006.01)

(52) U.S. Cl. .................. 604/541; 604/540; 604/543

(58) Field of Classification Search .................. 604/540, 604/541, 543, 544
See application file for complete search history.

(56) References Cited

U.S. PATENT DOCUMENTS

| | | | |
|---|---|---|---|
| 5,399,165 A | 3/1995 | Paul, Jr. | |
| 5,472,435 A | 12/1995 | Sutton | |
| 5,684,051 A | 11/1997 | Thompson | |
| 5,964,744 A | 10/1999 | Balbierz et al. | |
| 6,299,598 B1 | 10/2001 | Bander | |
| 6,368,356 B1 | 4/2002 | Zhong et al. | |
| 6,485,476 B1 | 11/2002 | Von Dyck et al. | |
| 7,037,288 B2 | 5/2006 | Rosenberg et al. | |
| 7,398,366 B2 * | 7/2008 | Ohran et al. | 711/162 |
| 7,591,834 B2 * | 9/2009 | Buckley et al. | 606/209 |
| 7,670,332 B2 * | 3/2010 | O'Keefe et al. | 604/544 |
| 7,722,677 B2 * | 5/2010 | Ward | 623/23.66 |
| 2002/0042562 A1 | 4/2002 | Meron et al. | |
| 2002/0091352 A1 * | 7/2002 | McGuckin et al. | 604/29 |
| 2005/0048121 A1 | 3/2005 | East et al. | |
| 2006/0167416 A1 | 7/2006 | Mathis et al. | |
| 2006/0188546 A1 | 8/2006 | Giroux | |
| 2007/0083154 A1 | 4/2007 | Sauvageau | |
| 2008/0051866 A1 | 2/2008 | Chen et al. | |

* cited by examiner

*Primary Examiner* — Lynne Anderson
(74) *Attorney, Agent, or Firm* — Brinks Hofer Gilson & Lione

(57) ABSTRACT

In at least one embodiment of the present invention, a drainage catheter for draining part of patient's body is provided. The catheter comprises an elongated member having a proximal portion extending to a distal portion and a lumen formed therethrough for fluid communication with the patient's body. The distal portion is formed of a polymer material having a first phase transition temperature and a second phase transition temperature that is less than the first phase transition temperature but is greater than about body temperature. The distal portion has a first configuration when at about body temperature for at least one of moving and anchoring the distal portion within the patient's body. The distal portion self-configures to a second configuration when at a temperature of at least the second phase transition temperature for retrieval of the distal portion from the patient's body.

19 Claims, 3 Drawing Sheets

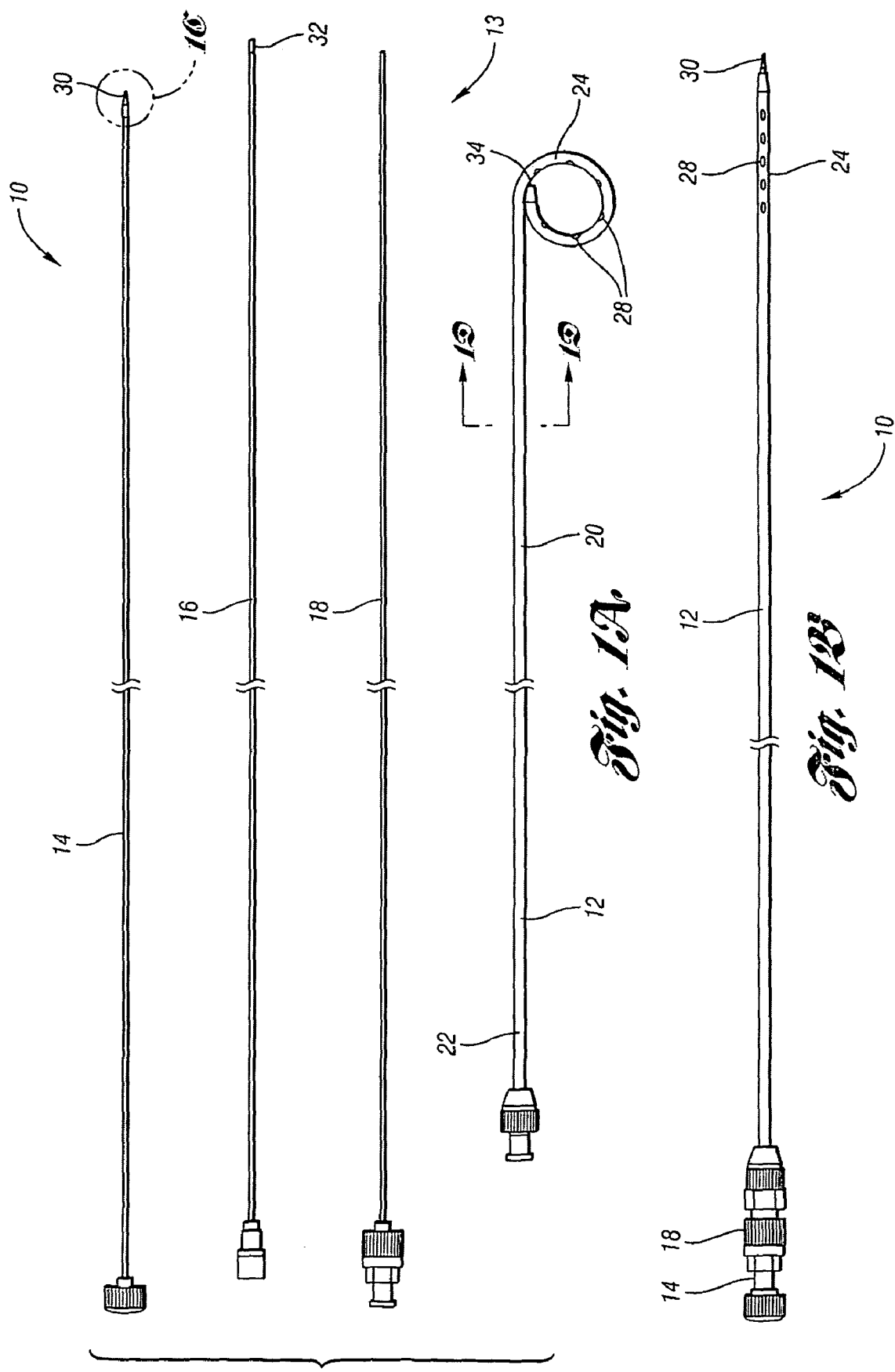

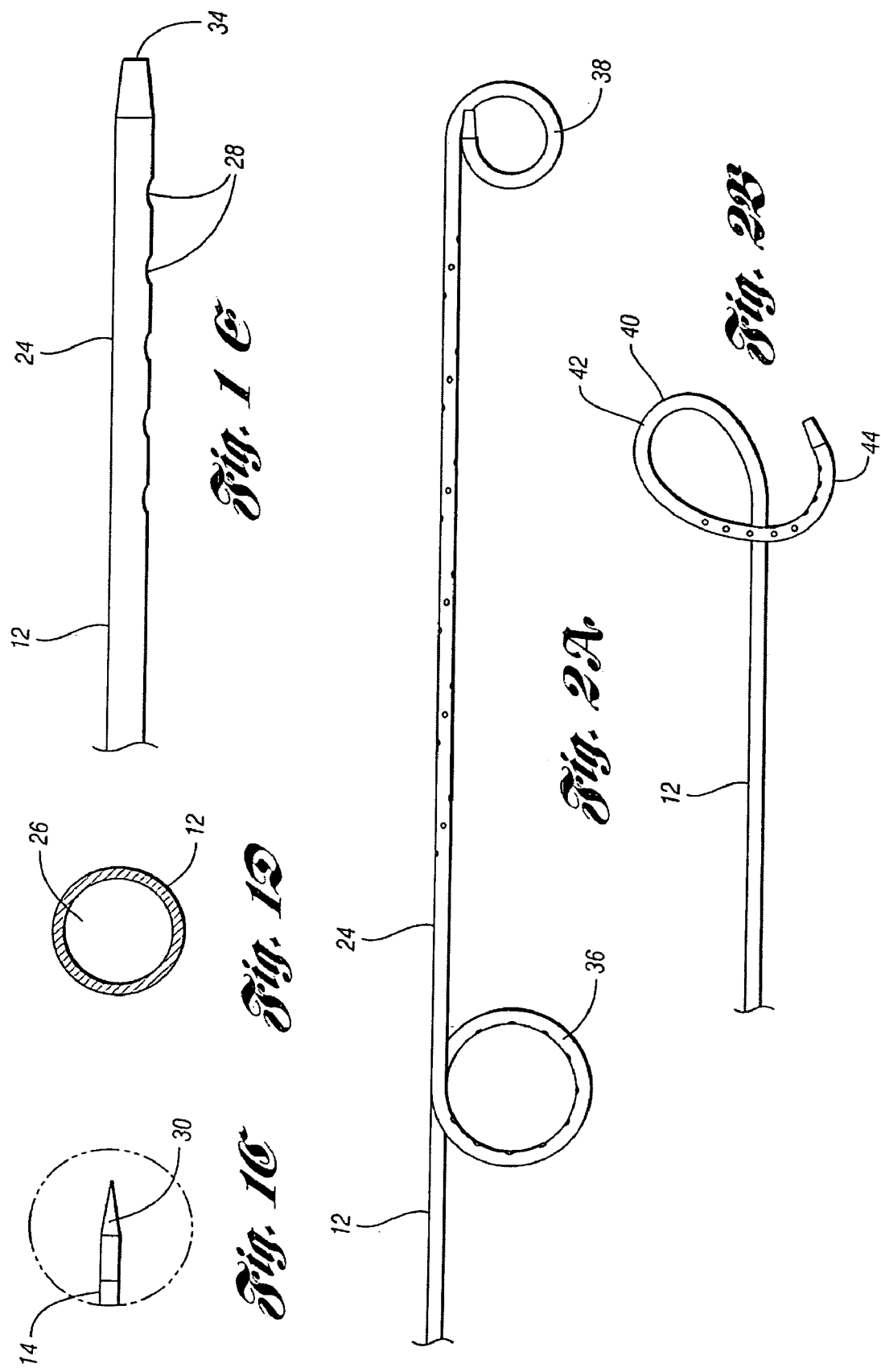

DRAINAGE CATHETER AND METHOD FOR CATHETERIZING A PATIENT

BACKGROUND OF THE INVENTION

Field of the Invention

The present invention relates generally to catheters and more specifically, to a drainage catheter having a distal end in a predetermined configuration for anchoring or positioning within a patient's body and a method for catheterizing the patient.

BACKGROUND

There are a variety of therapies or treatments that require a catheter with a distal anchor or the alike to position the catheter in a patient's body. One particular application involves catheters used for drainage purposes. Generally, these catheters are introduced into the patient over a trocar needle and/or guide wire. For example, the trocar needle may be used to gain access into the patient's body. The guide wire is placed through the needle and the needle may then be removed. The catheter, which is assembled with a stiffening cannula, is passed over the guide wire into the cavity. The cannula and guide wire can then be withdrawn leaving a portion of the catheter at its distal end in the desired cavity.

Various catheters have been developed with diverse anchor structures to prevent inadvertent removal of the catheter. One such anchor comprises a "pigtail loop" configuration of a distal flexible tube portion at or near the distal end of the catheter. Typically, the pigtail loop configuration is a "closed" configuration for anchoring and is manually uncurled to an "open" configuration for retrieval from the cavity. The pigtail loop configuration prevents accidental removal of the catheter from the patient. Generally, the pigtail loop is preformed in the flexible tube of the catheter. For introduction into a patient, a stiff cannula or similar implement is inserted through the catheter lumen to straighten the pigtail loop. The distal end of the flexible tube returns to the pigtail loop configuration after the cannula is removed. Typically, a "suture" thread, e.g., thin cable, or other filamentary member extends through two draw ports which are spaced opposite from each other along the distal portion of the flexible tube. These ports come into juxtaposition when the pigtail loop forms after the physician removes the cannula. Then the physician will take up any slack in the suture that leads proximally from the pigtail loop. When the suture is made taught, it holds the juxtaposed ports of the catheter together and thereby prevents the pigtail loop from straightening. While in the configuration, however, the suture may become encrusted, partially or fully preventing body fluids from draining through the catheter. For example, the catheter may drain body fluids such as urine or bile which may solidify and accumulate on the suture, thereby at least partially obstructing the lumen from draining the body fluids. In such a scenario, the catheter needs to be flushed out, for example, with a saline solution or if this is ineffective, the catheter needs to be switched out.

When it is appropriate to remove the catheter, a stiff cannula is inserted through the lumen with the suture still taught until the cannula reaches the pigtail loop. Thereafter, the tension on the suture is released before or while the stiff cannula is advanced distally to straighten the pigtail loop and facilitate the removal of the catheter from the patient. The cannula may however become entangled with the suture during this procedure, especially if the tension on the suture is not sufficient controlled. In this event, the interventionalist will need to further manipulate the cannula to free it from the suture so that the cannula may be advanced distally to straighten the pigtail loop. Accordingly, further improvements and enhancements are needed for anchoring and/or removing the catheter from the patient's body.

BRIEF SUMMARY OF THE INVENTION

In satisfying the above need and overcoming the above and other drawbacks and limitations of the known technology, the present invention provides a drainage catheter for draining part of a patient's body. The catheter comprises an elongated member having a proximal portion extending to a distal portion and a lumen formed therethrough for fluid communication with the patient's body. Forming the distal portion of the elongated member is a polymer material having a first phase transition temperature and a second phase transition temperature. The second phase transition temperature is less than the first phase transition temperature but is greater than about body temperature. The distal portion of the elongated member has a first configuration when at about body temperature for at least one of moving and anchoring the distal portion within the patient's body. When at a temperature of at least the second phase transition temperature, the distal portion of the elongated member self-configures to a second configuration for retrieval from the patient's body.

In one aspect, the polymeric material includes shape memory polymers having the first and second phase transition temperatures.

In at least one other embodiment of the present invention, a drainage catheterization kit for draining part of a patient's body is provided. The kit comprises the drainage catheter as discussed in the foregoing paragraphs and a trocar assembly. A cannula and a trocar stylet are included in the trocar assembly. The trocar stylet has a trocar tip for piercing through tissue of the patient's body. The cannula is configured to be positioned within the lumen of the catheter to reinforce the distal portion of the catheter for insertion into the patient's body. The trocar stylet is configured to be passed through the cannula to position the trocar tip distally from the distal portion of the catheter.

In at least one other embodiment of the present invention, a method for catheterizing a patient's body for drainage therefrom is provided. The method comprises moving and/or anchoring a distal portion of an elongated member of a drainage catheter within the patient's body. Polymeric material forms the distal portion of the elongated member and includes shape memory polymers having a first phase transition temperature and a second phase transition temperature. The second phase transition temperature is less than the first phase transition temperature but is greater than about body temperature. The distal portion is at about body temperature and is in a first configuration. Part of the patient's body is drained via a lumen formed through the catheter. The distal portion of the catheter is heated to at least the second phase transition temperature where the distal portion self-configures to a second configuration for retrieval from the patient's body.

Further objects, features, and advantages of invention will become apparent from consideration of the following description and the appended claims when taken in connection with the accompanying drawings.

BRIEF DESCRIPTION OF THE DRAWINGS

FIG 1a is an exploded view of a drainage catheterization kit in accordance with an embodiment of the present invention;

FIG 1b is a side view of a drainage catheterization kit in accordance with an embodiment of the present invention;

FIG 1c is an enlarged partial side view of the tip of the trocar stylet depicted in FIG 1a;

FIG 1d is a cross-sectional view of the drainage catheter depicted in FIG 1a;

FIG 1e is an enlarged side view of the distal portion of the drainage catheter depicted in FIG 1a in an open configuration;

FIG 2a is a partial side view of a drainage catheter in accordance with an embodiment of the present invention;

FIG 2b is a partial side view of a drainage catheter in accordance with another embodiment of the present invention;

DETAILED DESCRIPTION OF THE INVENTION

Figure 2C:
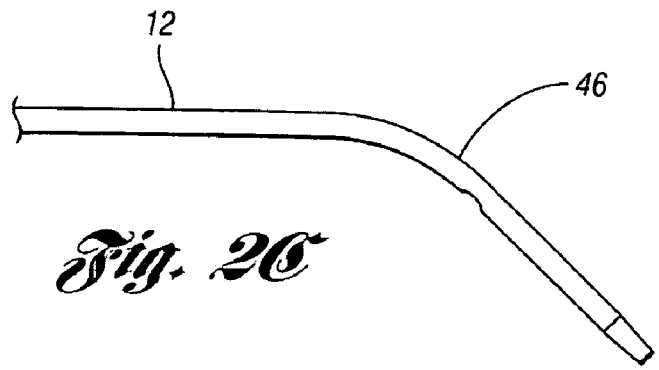
FIG 2c is a partial side view of a drainage catheter in accordance with one embodiment of the present invention.

Detailed embodiments of the present invention are disclosed herein. It is understood however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and for teaching one skilled in the art to practice the present invention.

The present invention seeks to overcome some of the problems associated with positioning and retrieving a drainage catheter within a patient's body that has a distal end in a predetermined configuration, e.g., curled or coiled configuration for anchoring therein. Preferably, the present invention provides a drainage catheter, which is at least partially formed of shape memory polymers, and a method for using the drainage catheter for catheterization which facilitates positioning and removing of the drainage catheter from the patient's body.

Shape memory polymers form polymeric material/s with the ability to sense and respond to external stimuli, e.g., temperature, pH, light, etc., in a predetermined way. Thermally induced shape memory polymers may exhibit a one-way shape memory effect due to their distinct thermal dynamics and polymer structures. Notably, this one-way memory effect differs from many shape memory alloys which can exhibit modulating shape memory effects due to the reversible nature of their grain microstructures, e.g., alternating between martensite and austenite repeatedly in response to repeated temperature changes.

In one example, shape memory polymers have polymer structures that can be considered as phase-segregated linear block copolymers having hard segments and soft segments. The hard segment, e.g., cross-linked, highly crystalline or semi-crystalline segment, acts as the frozen phase and the soft segment, e.g., amorphous or semi-crystalline segment, acts as the reversible phase. The reversible phase transformation of the soft segment is responsible for the shape memory effect. When the shape memory polymer is heated above the melting point ($T(m)$) or glass transition temperature ($T(g)$) of the hard segment, which is higher than the $T(m)$ or $T(g)$ of the soft segment, the material can be processed, e.g., molding, extrusion or the alike. This original shape can be memorized forming a remembered shape by cooling the shape memory polymer below the $T(m)$ or $T(g)$ of the hard segment. $T(m)$ is hereinafter understood to refer to the melting temperature or melting temperature range of the polymers (or polymer segments) where the polymer crystal lattice structures are no longer stable and/or free rotation and movement of the polymers (or polymer segments) readily occurs. $T(g)$ is hereinafter understood to refer to the glass transition temperature or glass transition temperature range, e.g., softening temperature, of the polymers (or polymer segments) where some free rotation and/or movement of the polymers (or polymer segments) can occur.

One method for forming a temporary shape is by deforming the material in the remembered shape at a temperature below the $T(m)$ or $T(g)$ of the hard segment but above the $T(m)$ or $T(g)$ of the soft segment and then cooling the material below the $T(m)$ or $T(g)$ of the soft segment to fix the deformed shape. The remembered or original shape is recovered by heating the shape memory polymer above the $T(m)$ or $T(g)$ of the soft segment, allowing at least some free rotation and/or movement of the soft segment for releasing the material from its temporary shape. Another method for setting the temporary shape involves the material in the remembered shape being deformed at a temperature lower than the $T(m)$ or $T(g)$ of the soft segment, resulting in stress and strain being absorbed by the soft segment. When the material is heated above the $T(m)$ or $T(g)$ of the soft segment, the stress and strains are relieved, e.g., via at least some free rotation and/or movement of the soft segment, and the material returns to its remembered shape. This is believed to be why the thermally induced shape memory polymers of the present invention have a one-way shape memory effect; they remember one permanent shape formed at the higher temperature, while many temporary shapes are possible at lower temperatures for which the systems do not have any memory because of the free rotation and/or movement of the soft segments.

The present invention employs polymeric material having shape memory properties to form at least the distal portion of the drainage catheter. Preferably, the temporary shape of the distal portion of the catheter is at least partially curled for positioning or anchoring in the patient's body and the remembered shape is an uncurled, open or substantially straightened configuration to facilitate removal of the drainage catheter from the patient's body. To remove the drainage catheter, the distal portion in its temporary shape is heated or warmed to return the distal portion to its remembered shape and the interventionalist pulls the catheter out from the patient's body.

Referring to FIGS. 1a-1e, a drainage catheterization kit in accordance with the present invention is provided. The kit 10 is for draining part of a patient's body and includes a drainage catheter 12 and a trocar assembly 13. The drainage catheter 12 has an elongated member 20 with a proximal portion 22 extending to a distal portion 24. A lumen 26 is formed through the catheter 12 extending between the proximal portion 22 and the distal portion 24.

A distal portion 24 of the catheter 12 is made from polymeric material which is preferably compliant and kink resistant, e.g., soft and elastomeric. In one example, the entire elongated member 20 is made from the same polymeric material or resin, e.g., by an extrusion process, pultrusion process or the alike. In another example, the elongated member is made from at least two polymeric materials or resins, e.g., by co-extrusion, two shot molding or the alike. For instance, the elongated member 20 may be co-extruded from two polymeric resins where a first polymeric resin is extruded to form the distal portion 24 and the second polymeric resin is extruded to form the remaining portion of the elongated member 20.

In at least one embodiment, the polymeric material, which is used to form the distal portion 24, is comprised of shape memory polymers. Some examples of suitable polymers which may be formulated or polymerized to have shape memory effects are polyurethanes, polyester-urethanes, polyether-urethanes, polyesters, polyester-ethers, polyvinyl chlorides, silicones and polyvinyl alcohols. The polymeric material may include one of these types of polymers or these polymers may be blended or mixed to preferably form a relatively low flexural modulus material with suitable kink resistant properties and shape memory.

In one embodiment, the polymeric material has a first phase transition temperature, e.g., T(m) or T(g) of the hard segments of the shape memory polymers, and a second phase transition temperature, e.g., T(m) or T(g) of the soft segments of the shape memory polymers. The second phase transition temperature is less than the first phase transition temperature but is greater than about body temperature. Body temperature is typically about 98.6° F. but may vary slightly depending on the wellbeing of the patient. In one example, the first phase transition temperature is greater than about 108° F. In another example, the second phase transition temperature is less than about 108° F. and is preferably in the range of 103° F.-108° F.

The distal portion 24 of the catheter 12 has a first configuration when at about body temperature. That is, the first configuration is the temporary shape. The first configuration is for positioning the distal portion 24 within the patient's body, e.g., anchoring the distal portion 24 within the body. FIG 1a illustrates the distal portion 24 in a "closed" pigtail loop configuration, which is one example for the first configuration. In this scenario, the distal portion 24 is preferably stiff enough at body temperature to prevent straightening of the pig tail loop and sufficiently anchors the drainage catheter 12 within the body without the use of a tensioning suture or other filamentary member. However, the distal portion 24 is also preferably compliant enough to be kink resistant and accordingly, the material properties of the polymeric material may be balanced so as to satisfy both of these conflicting performance criteria.

In at least one embodiment of the present invention, the distal portion 24 self-configures to a second configuration when at a temperature of at least the second phase transition temperature due to the shape memory properties of the polymeric material. That is, the second configuration is the remembered shape. The second configuration preferably has a shape that facilitates removal of the drainage catheter 12 from the patient's body. FIG 1e illustrates the distal portion 24 in an "open" or uncurled and substantially straightened configuration, which is one example for the second configuration. Moreover, the distal portion 24 is preferably more flexible in the second configuration than in the first configuration which may further facilitate its removal from the patient's body. It is believed that there is a reduction in the stiffness of the distal portion 24 in the second configuration because: (1) the flexural modulus of the polymeric material steadily decreases as the temperature increases from body temperature to the second phase transition temperature and (2) the soft segments of the shape memory polymers become more mobile at the second phase transition temperature further reducing the flexural modulus of the polymeric material.

In one embodiment, the polymeric material includes a second plurality of polymers which are mixed or blended with the first plurality of shape memory polymers. The second plurality of polymers may also be shape memory polymers but which have a different phase transition temperature, i.e., third phase transition temperature, for the corresponding soft segments than do the first plurality of shape memory polymers. Preferably, the third phase transition temperature is less than the second phase transition temperature but is greater than about room temperature. Room temperature may be considered between about 70 and 72° F. In one example, the third phase transition temperature is in the range of about 88° F. to body temperature.

The distal portion 24 may have a third configuration, e.g., a second temporary shape, when at about room temperature. The third configuration may be for inserting the distal portion 24 in the patient's body. In one example, the distal portion 24 self-configures from the third configuration to the first configuration when at a temperature of at least the third phase transition temperature due to the shape memory properties of the polymeric material. That is, the third configuration is a second temporary shape and the first configuration is the first temporary shape. Moreover, the distal portion 24 may be similarly configured in the third configuration as in the second configuration, such as for example, as illustrated in FIG 1e. Accordingly, the distal portion 24 may have a substantially straight configuration for being inserted into the patient's body, preferably without a stiffening cannula, a pigtail loop configuration for anchoring within the patient's body, preferably without a tensioning suture, and a substantially straight configuration for being removed from the patient's body, preferably without a stiffening cannula.

The distal portion 24 of the drainage catheter 12 may also have a plurality of apertures 28 formed therein that are in fluid communication with the lumen 26. Body fluid flows from the patient's body through the apertures 28 and further through the lumen 26 to the proximal portion 22 of the catheter 12 for removal from the patient.

The trocar assembly 13 includes a cannula 18 and a trocar stylet 14. The cannula 18 is elongated and has an outer diameter that is sized to fit within the lumen 26 of the catheter 12. The cannula may be made of metal or any other suitably stiff material known to those skilled in the art. The cannula is positioned within the lumen 26 to reinforce the distal portion 24 of the catheter 12 for insertion into the patient's body.

The trocar stylet 14 has a distal trocar tip 30 (see FIG 1c for an enlarged view), which is preferably pointed or beveled, for piercing through, e.g., cutting, digging or poking through, the body tissue of the patient. The trocar stylet 14 is also elongated and has an outer diameter that is sized to fit within the cannula 18. As illustrated in FIG 1b, the trocar stylet 14 is passed through the cannula 18, which is passed through the catheter 12, to position the trocar tip 30 distally from the distal portion 24 of the catheter 12. In this configuration, the interventionalist introduces the drainage catheter 12 into the patient by manipulating the trocar tip 30 to pierce through the patient's body tissue to place the distal portion 24 at an intended location.

The trocar assembly 13 may also include an obturator 16 which is used to straighten the catheter 12 (inside the cannula 18). The blunt obturator 16 is then removed from the cannula 18 and replaced with the trocar stylet 14. The obturator 16 is elongated and is sized to fit within the cannula 18. The obturator 16 is made from a suitably stiff material and may be passed through the cannula 18 to position its blunt tip 32 within the distal portion 24 of the drainage catheter 12, obstructing the apertures 28 and/or a distal opening 34 of the drainage catheter 12.

The kit 10 may further comprise a flexible stiffener (not shown) which may be used in lieu of the cannula 18 and/or trocar stylet 14 and/or the obturator 16 for inserting the catheter 12 into the patient. The flexible stiffener may be made from a stiff plastic or other suitable material and is configured to be positioned within the lumen 26 of the catheter 12 to reinforce/straighten the distal portion 24 of the catheter 12 for insertion into the patient's body.

Figure 2D:
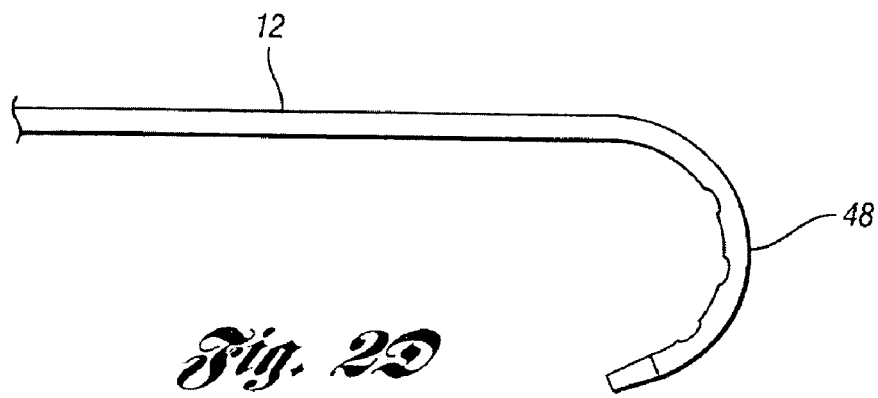
FIG 2d is a partial side view of a drainage catheter in accordance with another embodiment of the present invention.

Referring to FIGS. 2a-2d, alternative configurations for the distal portion 24 are illustrated by way of example and are not intended to limit the scope of the present invention. FIG 2a illustrates the distal portion 24 having multiple loops 36 and 38 for anchoring the drainage catheter 12 within the patient. FIG 2b illustrates the distal portion 24 having a loop 40 with a closed portion 42 and a distally extending open portion 44. FIG 2c illustrates the distal portion 24 with an open bent end 46 which may facilitate moving the distal portion 24 within the body of the patient to an intended location. FIG 2d illustrates the distal portion 24 with an open curled end 48 which may facilitate moving and/or anchoring the distal portion 24 within the patient.

Figure 3:
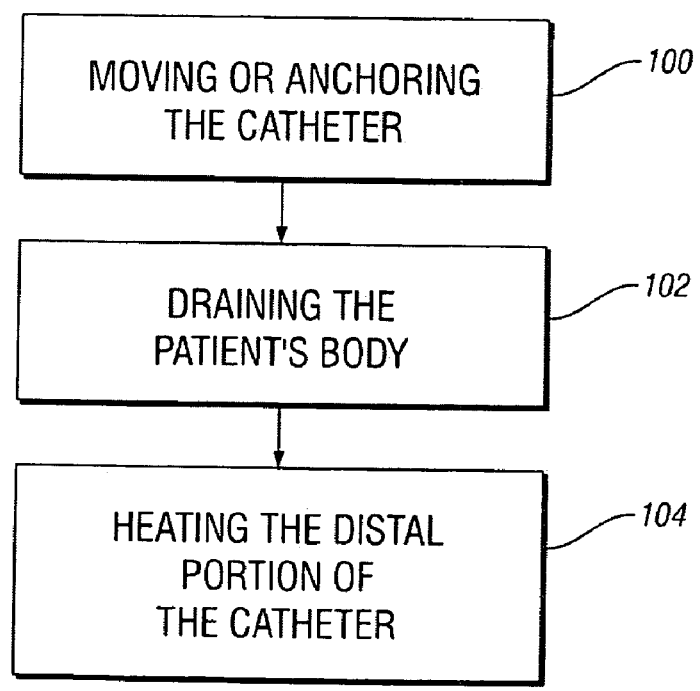
FIG 3 is a flow chart of a method for catheterizing a patient's body for drainage in accordance with one example of the present invention.

Referring to FIG 3, a method for catheterizing a patient's body for drainage therefrom in accordance with an example of the present invention is provided. The method comprises moving and/or anchoring a distal portion of an elongated member of a drainage catheter at 100 within the patient's body. The distal portion is formed of a polymeric material including shape memory polymers having a first phase transition temperature and a second phase transition temperature. The second phase transition temperature is less than the first phase transition temperature but is greater than about body temperature. The distal portion is at about body temperature and is in a first configuration.

The drainage catheter has a lumen formed therethrough. A part of the patient's body is drained at 102 via the lumen.

The distal portion of the catheter is heated at 104 to at least the second phase transition temperature. The distal portion self-configures to a second configuration which facilitates retrieving the drainage catheter from the patient's body. In one example, the distal portion is heated by flushing and/or advancing a warm fluid through the lumen to the distal portion, such as for example, a saline solution warmer than body temperature.

In another example, the method further comprises inserting the distal portion of the catheter into the patient's body. The polymeric material includes a second plurality of polymers having a third transition temperature, which is less than the second phase transition temperature but is greater than about room temperature. The second plurality of polymers may be shape memory polymers or the alike. The distal portion is at about room temperature and is the third configuration. The distal portion is then warmed, e.g., via body fluid at body temperature, to at least the third phase transition temperature whereby the distal portion self-configures to the first configuration.

As a person skilled in the art will readily appreciate, the above description is meant as an illustration of the implementation of the principles of the invention. This description is not intended to limit the scope for application of this invention in that the invention is susceptible to modification, variation, and change, without departing from the spirit of this invention as defined in the following claims.

What we claim is:

1. A drainage catheter for draining part of a patient's body, the catheter comprising:
    an elongated member having a proximal portion extending to a distal portion and a lumen formed therethrough for fluid communication with the patient's body, the distal portion formed of a polymeric material including a first plurality of shape memory polymers having a first phase transition temperature and a second phase transition temperature less than the first phase transition temperature but greater than about 98.6 degrees Fahrenheit, the distal portion having a first configuration when at about 98.6 degrees Fahrenheit for at least one of moving and anchoring the distal portion within the patient's body and self-configures to a second configuration when at a temperature of at least the second phase transition temperature for retrieval of the distal portion from the patient's body.

2. The catheter of claim 1 wherein the first plurality of shape memory polymers comprises polyurethanes, polyester-urethanes, polyether-urethanes, polyesters, polyester-ethers, polyvinyl chlorides, silicones, polyvinyl alcohols or a mixture thereof.

3. The catheter of claim 1 wherein the first phase transition temperature is greater than about 108° F. and the second phase transition temperature is less than about 108° F.

4. The catheter of claim 1 wherein the second phase transition temperature is in the range of about 103 to 108° F.

5. The catheter of claim 1 wherein the polymeric material further includes a second plurality of polymers having a third phase transition temperature less than the second phase transition temperature but greater than about room temperature, the distal portion having a third configuration when at about the room temperature for inserting the distal portion into the patient's body and self-configures to the first configuration when at a temperature of at least the third phase transition temperature.

6. The catheter of claim 5 wherein the third phase transition temperature is at least about 88° F.

7. The catheter of claim 1 wherein the first configuration is defined by a first shape of the distal portion while being cooled through the first phase transition temperature and the second configuration is defined by deforming the first configuration while one of being at a temperature below the second phase transition temperature and being cooled through the second phase transition temperature.

8. The catheter of claim 1 wherein the first configuration has at least a partially curled shape.

9. The catheter of claim 8 wherein the second configuration has an uncurled shape relative to the shape of the first configuration.

10. The catheter of claim 1 wherein the distal portion is more flexible when in the second configuration than in the first configuration to facilitate retrieval of the distal portion from the patient's body.

11. A drainage catheterization kit for draining part of a patient's body, the kit comprising:
    a drainage catheter including:
        an elongated member having a proximal portion extending to a distal portion and a lumen formed therethrough for fluid communication with the patient's body, the distal portion formed of a polymeric material including a first plurality of shape memory polymers having a first phase transition temperature and a second phase transition temperature less than the first phase transition temperature but greater than about 98.6 degrees Fahrenheit, the distal portion having a first configuration when at about 98.6 degrees Fahrenheit for at least one of moving and anchoring the distal portion within the patient's body and self-configures to a second configuration when at a temperature of at least the second phase transition temperature for retrieval of the distal portion from the patient's body; and a trocar assembly including a cannula and a trocar stylet having a trocar tip for piercing through tissue of the patient's body, the cannula configured to be positioned within the lumen of the elongated member to reinforce the distal portion for insertion into the patient's body and the trocar stylet configured to be passed through the cannula to position the trocar tip distally from the distal portion.

12. The kit of claim 11 wherein the trocar assembly further includes an obturator configured to be positioned within the cannula to facilitate straightening of the distal portion of the catheter.

13. The kit of claim 11 further comprising a flexible stiffener configured to be positioned within the lumen of the elongated member to reinforce the distal portion for insertion into the patient's body over a guide wire.

14. The kit of claim 11 wherein the first phase transition temperature is greater than about 108° F. and the second phase transition temperature is less than about 108° F.

15. The kit of claim 11 wherein the second phase transition temperature is in the range of about 103 to 108° F.

16. The kit of claim 11 wherein the polymeric material further includes a second plurality of polymers having a third phase transition temperature less than the second phase transition temperature but greater than about room temperature, the distal portion having a third configuration when at about the room temperature for inserting the distal portion into the patient's body and self-configures to the first configuration when at a temperature of at least the third phase transition temperature.

17. The kit of claim 16 wherein the third phase transition temperature is at least about 88° F.

18. The kit of claim 11 wherein the first configuration has at least a partially curled shape.

19. The kit of claim 18 wherein the second configuration has an uncurled shape relative to the shape of the first configuration.

* * * * *